United States Patent
Taniguchi et al.

[11] Patent Number: 5,935,398
[45] Date of Patent: Aug. 10, 1999

[54] HYDROCARBON SENSOR

[75] Inventors: Noboru Taniguchi, Osaka; Yasushi Nakagiri, Tsuzuki-gun; Takaharu Gamou, Fujiidera; Katsuyuki Ohara, Katano; Masahiro Kawamura, Takatsuki, all of Japan

[73] Assignee: Matsushita Electric Industrial Co., Ltd., Osaka, Japan

[21] Appl. No.: 08/740,753

[22] Filed: Nov. 1, 1996

[30] Foreign Application Priority Data

Nov. 2, 1995 [JP] Japan ................................ 7-285800

[51] Int. Cl.$^6$ ........................................... G01N 27/26
[52] U.S. Cl. .......................... 204/424; 204/421; 204/426; 422/98; 422/94; 73/19.01; 73/23.31; 73/31.06
[58] Field of Search ........................ 204/421, 426, 204/422, 424; 422/98, 94; 73/19.01, 23.31, 31.06

[56] References Cited

U.S. PATENT DOCUMENTS

| | | | |
|---|---|---|---|
| 4,598,576 | 7/1986 | Goldsmith et al. | 73/19 |
| 4,718,991 | 1/1988 | Yamazoe et al. | 204/421 |
| 5,387,330 | 2/1995 | Taniguchi et al. | 204/421 |
| 5,439,579 | 8/1995 | Koide et al. | 204/422 |

FOREIGN PATENT DOCUMENTS

| | | |
|---|---|---|
| 0677741 A2 | 10/1995 | European Pat. Off. . |
| 06242060 | 2/1994 | Japan . |
| 7-167833 | 7/1995 | Japan . |
| 2206571 | 1/1989 | United Kingdom . |
| WO 95/14226 | 5/1995 | WIPO . |

OTHER PUBLICATIONS

Hiroyasu Iwahara, "Technological chanllenges in the application of proton conducting ceramics", Solid State Ionics, 77 (1995), pp. 289–298. No month available.
Search Report, May 20, 1998.
Collected Papers of Spring Meeting of Japan Electrochemical Society, 1994. No month available.
Collected Paper of Fall Meeting of Japan Sensor Association, 1995. No month available.

*Primary Examiner*—Bruce F. Bell
*Attorney, Agent, or Firm*—Ratner & Prestia

[57] ABSTRACT

A hydrocarbon sensor of solid type has a pair of electrodes, and a proton conductive solid electrolyte of a barium-cerium oxide, for example, a rare earth element at least in the third element.

13 Claims, 9 Drawing Sheets

HYDROCARBON SENSOR

BACKGROUND OF THE INVENTION

1. Field of the Invention

The present invention relates to a hydrocarbon sensor for detecting hydrocarbon and measuring its concentration in a temperature range from room temperature to high temperature (800° C.) that can be used for combustion control (clean burn) of combustion engine and appliance, for detecting hydrocarbon in exhaust gas from automotive engine, stove, and catalytic combustion appliance, by detection of hydrocarbon in the living environments.

2. Related Art of the Invention

As the method for measuring or detecting hydrocarbons, roughly classified by material, the semiconductor type and electrolyte type are known. In the semiconductor type using $TiO_2$, $SnO_2$, and the like, a semiconductor material is blended with a catalytic active material in order to react with CO and other reducing gas and to add selectivity. For combustion with catalyst, however, the atmosphere requires oxygen, and the hydrocarbon concentration cannot be detected correctly in oxygen-free state or in the atmosphere varying in the oxygen concentration.

The type using electrolyte, on the other hand, requires an excellent proton conductor. For use in combustion engine and appliance, a proton conductor of oxide usable at room temperature or higher is needed. Recently, as proton conductor of oxide, $CaZr_{0.9}In_{0.1}O_{3-\alpha}$ oxide is developed, and it is attempted to be applied in hydrocarbon sensor.

As the hydrocarbon sensor using solid electrolyte of calcium-zirconium oxide as far as known at the present, the electromotive force type using Pd-Au electrode (Nagoya University) <reference, Collected papers of spring meeting of Japan Electrochemical Society, 1994>, and the limit current detection type using porous alumina as diffusion rate determining layer (Toyota Central Research Institute) <reference, Collected paper of fall meeting of Japan Sensor Association, 1995> are known. However, the proton conductivity of solid electrolyte of calcium-zirconium oxide is as small as $5 \times 10^{-4}$ S/cm at 600° C., and in order to raise the sensor sensitivity, in the electromotive force type, the operating temperature must be set at high temperature of 700° C., or in the current detection type, it is difficult to use unless the film is made thin, and a solid electrolyte material of a higher proton conductivity has been demanded.

As for detecting mechanism and structure, in the electromotive force type, since the catalytic function of electrode is utilized, accurate detection of hydrocarbon is not expected in oxygen-free state or in the atmosphere of large concentration changes of oxygen. In the current type using alumina porous matter in the diffusion rate determining layer, it is hard to set the electrolyte voltage of hydrocarbon. Thus, various problems are involved in the prior arts.

That is, as the detector of hydrocarbons in living environments, or the hydrocarbon concentration detector of combustion exhaust gas from automotive engine, stove and other combustion appliance, there is an increasing demand for small, handy, and inexpensive sensor that is selective, and high in sensitivity and reliability in any atmosphere (free from effects of oxygen concentration). The sensor using calcium-zirconium oxide is small in proton conductivity, and a solid electrolyte having a higher proton conductivity is needed for smaller size, easier use, and higher sensitivity. Considering the detection characteristic, the method and mechanism for detecting hydrocarbons only accurately in any ambient environments are demanded.

SUMMARY OF THE INVENTION

Considering such conventional problems, it is hence an object of the invention to realize a small, handy, and inexpensive hydrocarbon sensor that is selective, and high in sensitivity and reliability in any atmosphere (free from effects of oxygen concentration).

In the light of the above problems, the invention presents a hydrocarbon sensor characterized by using barium-cerium oxide of high proton conductivity as solid electrolyte, and preferably the barium-cerium oxide contains a rare earth element at least in the third element. To detect hydrocarbons only accurately, in the hydrocarbon sensor of current detection type comprising a pair of electrodes, proton conductor, and hydrocarbon diffusion rate determining layer, it is intended to present a sensor having one electrode being active to hydrogen and having proton diffusion rate determining function, and the electrode having the proton diffusion rate determining layer contains at least one element selected from the group consisting of the elements Pd, Ag, Pt, Ru, Ti, V, Ca, Mg, Mn, Cu, Ni, Zi, and La. Moreover, in order to detect in any atmosphere such as oxygen-free state, a hydrocarbon sensor characterized by comprising hydrogen generating or moving element is proposed.

By executing the above means, it is possible to fabricate a small, handy, and inexpensive sensor that is selective, and high in sensitivity and reliability in any atmosphere (free from effects of oxygen concentration).

The hydrocarbon sensor of the invention is usable as hydrocarbon detector in living environments, and as hydrocarbon concentration detector of combustion exhaust gas from automotive engine, stove and other combustion appliance, in a temperature range from room temperature to high temperature (800° C.).

[REFERENCE NUMERALS]

Figure 1:
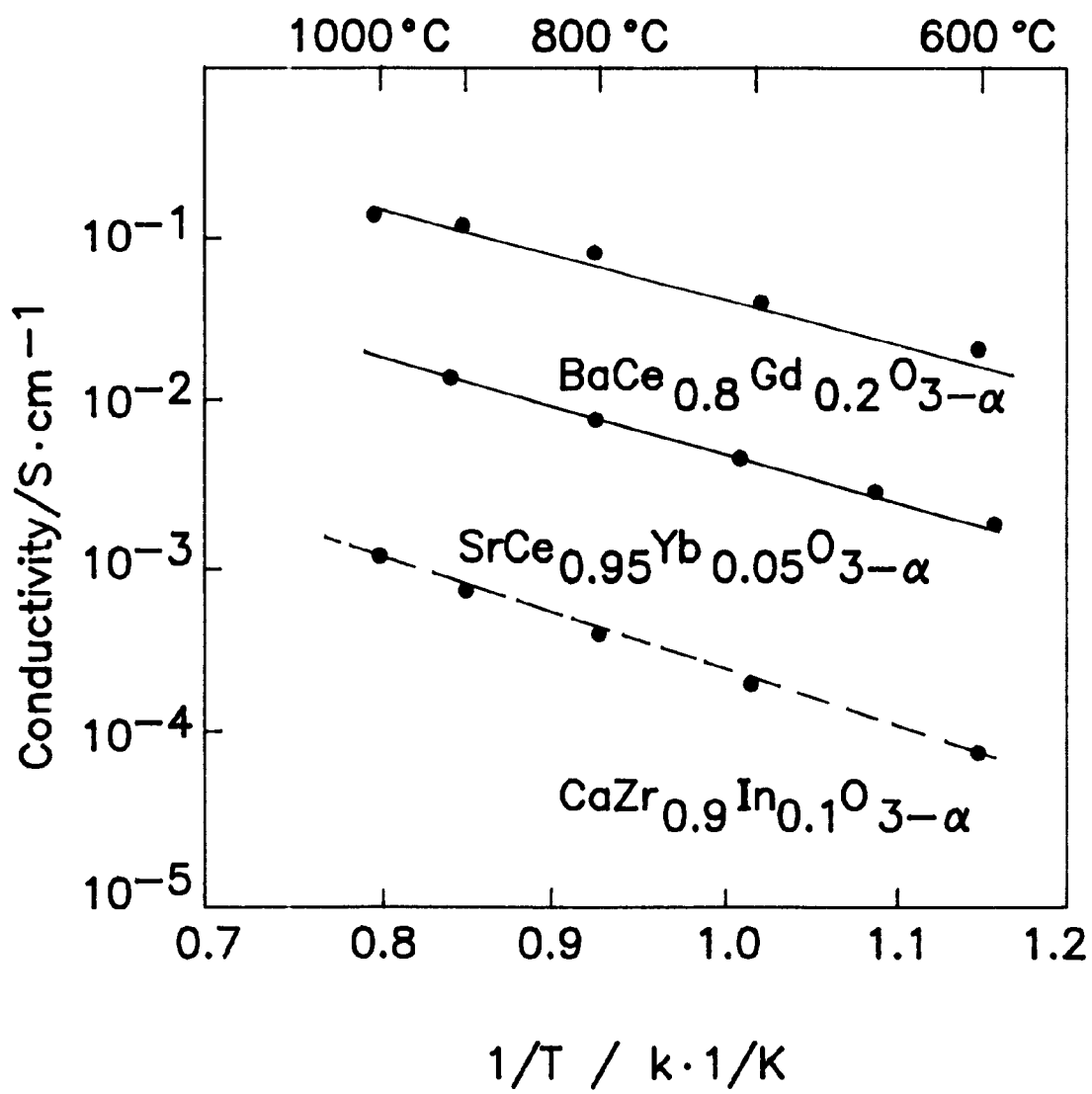
FIG. 1 is a diagram of ion conductivity in hydrogen atmosphere of barium-cerium oxide.

1 Solid electrolyte
2 Hydrocarbon active electrode (working electrode)
3 Inert electrode (counter electrode)
4 Heater 5 Anode
6 Cathode
7 Forsterite substrate composing diffusion rate determining layer
8 Glass
9 Anode having proton diffusion rate determining function
10 Platinum cathode
11 Hydrocarbon active electrode
12 Inert electrode
13 Proton conductive solid electrolyte of hydrogen pump
14 Pair of platinum electrodes

PREFERRED EMBODIMENTS OF THE INVENTION

[Embodiment 1]

This embodiment is an example of electromotive force type hydrocarbon sensor using a barium-cerium oxide as solid electrolyte.

FIG. 1 shows the ion conductivity of barium-cerium oxide in hydrogen atmosphere, in comparison between calcium-zirconia oxide and strontium-cerium oxide. As shown in the diagram, the proton conductivity of barium-cerium oxide is known to be higher than that of other materials. Using this material, an electromotive force sensor was actually fabricated, and high sensitivity sensing of hydrocarbon and operation at low temperature were investigated.

Figure 2:
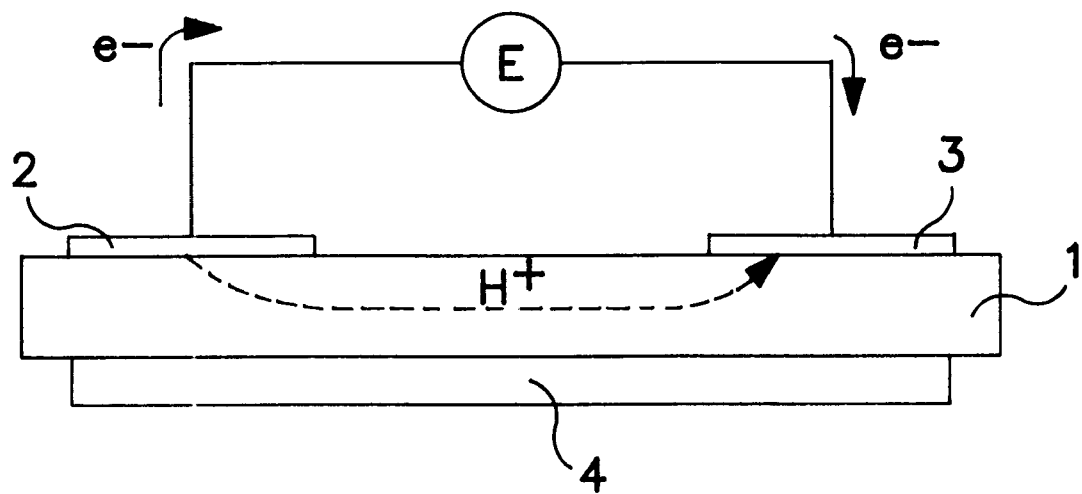
FIG. 2 is a structural diagram of an electromotive force type hydrocarbon sensor in an embodiment of the invention.

FIG. 2 shows a structure of an electromotive force type hydrocarbon sensor of the invention. In this sensor, a solid electrolyte 1 is composed of $BaCe_{0.8}Gd_{0.2}O_{3-\alpha}$ sinter of 10 mm×10 mm×0.5 mm thick, a hydrocarbon active electrode (working electrode) 2 of palladium (baking), and an inert electrode (counter electrode) 3 of gold (baking), and the sensor element is designed to be heated by a heater 4.

Figure 3:
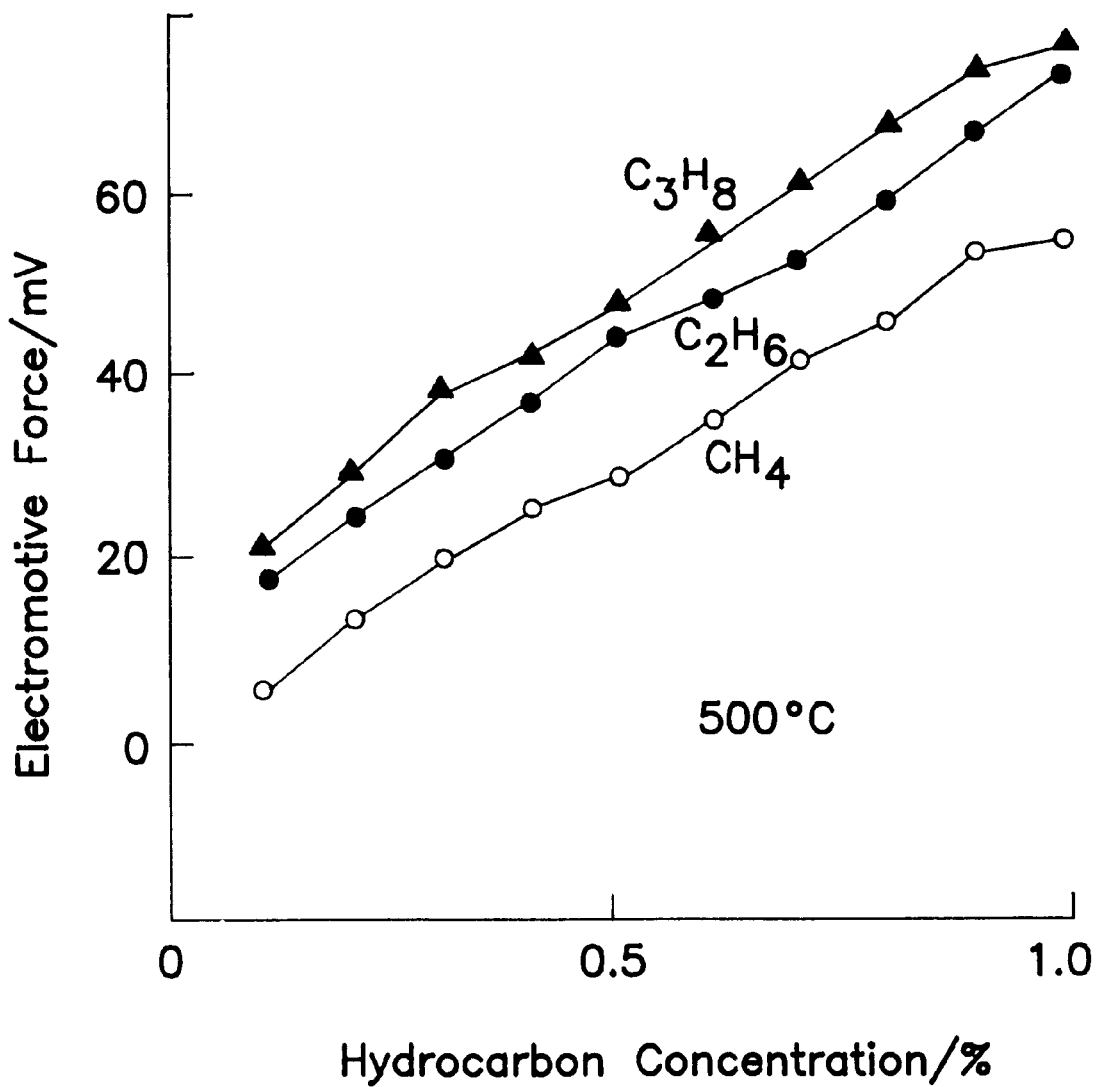
FIG. 3 is a diagram showing the relation of gas concentration and electromotive force at 500° C. of the sensor in the embodiment of the invention.

Hydrocarbon gas reacts with oxygen in the active electrode 2, and steam is generated. On the other hand, in the inert electrode 3, no reaction takes place, and an electromotive force due to steam contrast occurs between the active electrode 2 and inert electrode 3. At this time, in the solid electrolyte, the proton is a charge carrier Using methane, ethane and propane diluted in air as sample gas, each gas was passed through the sensor of the embodiment at flow velocity of 200 cc/min. Varying the gas concentration, the electromotive force to the concentration at various temperatures was investigated. FIG. 3 shows the relation of gas concentration and electromotive force at 500° C. In a gas concentration range of 0 to 1%, the electromotive force changed linearly in any gas, and this sensor was proved to work favorably at 500° C. The response was also excellent, and it was about 10 seconds in 90% response. When using calcium-zirconia oxide as the solid electrolyte, incidentally, at low temperature of 500° C., since the proton conductivity was small, the electromotive force was unstable relatively to the concentration. Hence, obviously, the electromotive force type hydrocarbon sensor using barium-cerium oxide as solid electrolyte of the invention operated favorably, and was found to be high in sensitivity as compared with the calcium-zirconia derivatives.

In this embodiment, palladium was used in the active electrode and gold in the inert electrode, but platinum may be used in the active electrode and copper in the inert electrode, or different combinations may be employed. Moreover, the shape and fabricating method of electrolyte and electrodes are not limited.

[Embodiment 2]

This embodiment is an example of current detection type hydrocarbon sensor of constant potential electrolytic type using barium-cerium oxide in the solid electrolyte.

Figure 4:
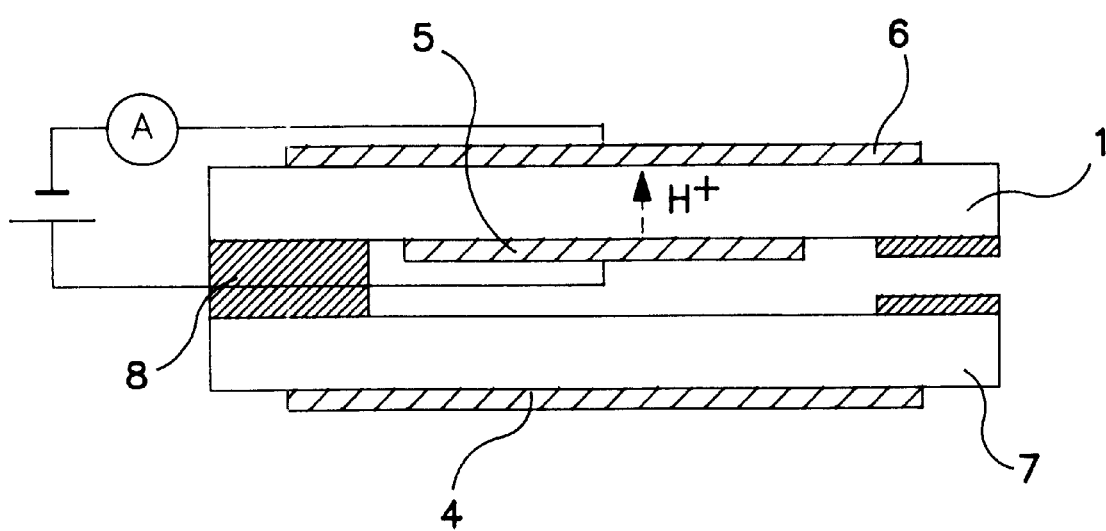
FIG. 4 is a structural diagram of a current detection type hydrocarbon sensor in other embodiment of the invention.

FIG. 4 shows a structure of the current detection type hydrocarbon sensor of the invention. In this sensor, a solid electrolyte 1 is composed of $BaCe_{0.8}Y_{0.2}O_{3-\alpha}$ (sinter of 10 mm×10 mm×0.5 mm thick, an anode 5 and a cathode are baked platinum electrodes, and the hydrocarbon diffusion rate determining layer is fabricated of forsterite substrate 7 and glass 8. This sensor element is designed to be heated by a heater 4.

The hydrocarbon passes through a diffusion rate determining path formed of forsterite and glass, and is dissociated into protons by electrolysis in the anode, conducts through proton conductive solid electrolyte, and is released as hydrogen through the cathode. At this time, an electric current flows in proportion to the proton moving amount, and a limit current flows depending on the hydrocarbon amount (concentration) of which diffusion is determined by rate.

Figure 5:
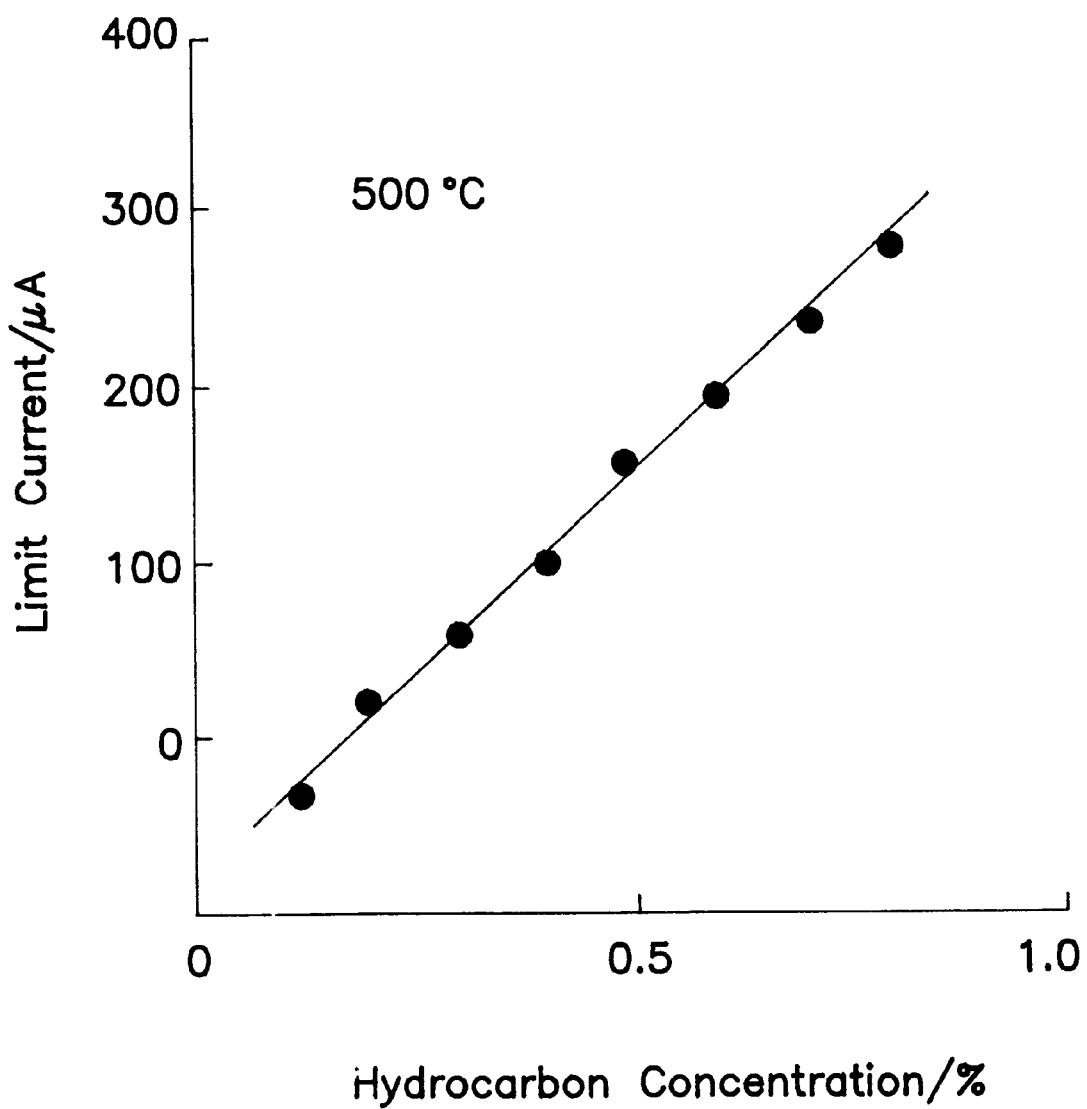
FIG. 5 is a diagram showing the relation of gas concentration and limit current at 500° C. of the sensor in the embodiment of the invention.

Same as in the preceding embodiment, methane, ethane, and propane diluted in air were used as sample gas, and passed into the sensor at a flow velocity of 200 cc/m. Varying the gas concentration, the limit current to concentration was investigated at various temperatures. FIG. 5 shows the relation of gas concentration and limit current at 500° C. In a gas concentration range of 0 to 1%, the limit current changed linearly in any gas, and this sensor was proved to work favorably at 500° C. The response was also excellent, and it was about 10 seconds in 90% response. When using calcium-zirconia oxide as the solid electrolyte, incidentally, at low temperature of 500° C., since the proton conductivity was small, the current was too small to be detected. Hence, obviously, the current detection type hydrocarbon sensor of constant potential electrolytic type using barium-cerium oxide as solid electrolyte of the invention operated favorably, and was found to be high in sensitivity as compared with the calcium-zirconia derivatives.

In this embodiment, the diffusion rate determining layer was fabricated by using ceramic substrate and glass, but the diffusion rate determining layer may be composed of a porous ceramic substrate or a single-pore substrate. In the embodiment, platinum is used as electrode material, but palladium or other material may be used. Moreover, the shape and fabricating method of electrolyte and electrodes are not limited.

[Embodiment 3]

This embodiment relates to an example of sensor having one electrode active to hydrogen and functioning to determine the proton diffusion rate, in a current detection type hydrocarbon sensor comprising a pair of electrode, proton conductor, and hydrocarbon diffusion rate determining layer.

Figure 6:
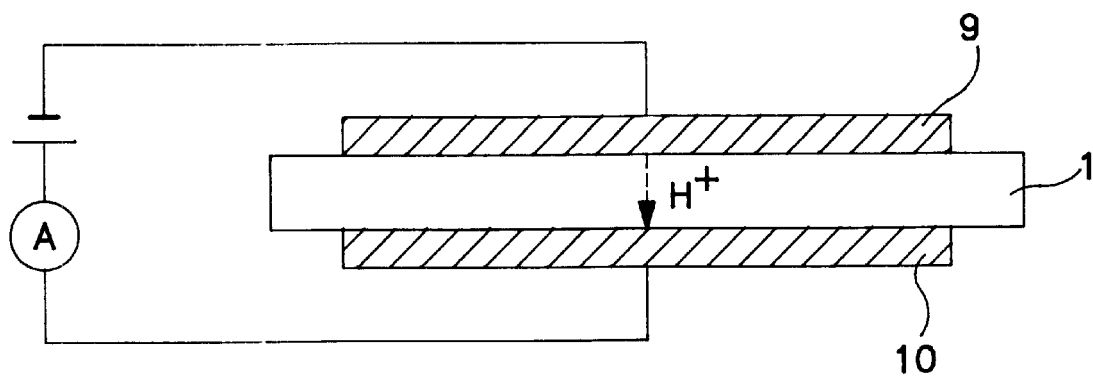
FIG. 6 is a structural diagram of a sensor in embodiment 3 of the invention.

In the sensor structure, as shown in FIG. 6, a solid electrolyte 1 is composed of $CaZr_{0.1}In_{0.1}O_{3-\alpha}$ sinter of 10 mm×10 mm×0.5 mm thick, an anode 9 is made of Ag-Pd electrode having proton diffusion rate determining function, and a cathode 10 is made of platinum. This sensor element is heated by an external heater 4. This structure does not require diffusion rate determining layer, and is hence much simplified.

Same as in the preceding embodiments, methane, ethane, and propane diluted in air were used as sample gas, and passed into the sensor at a flow velocity of 200 cc/m.

Figure 7:
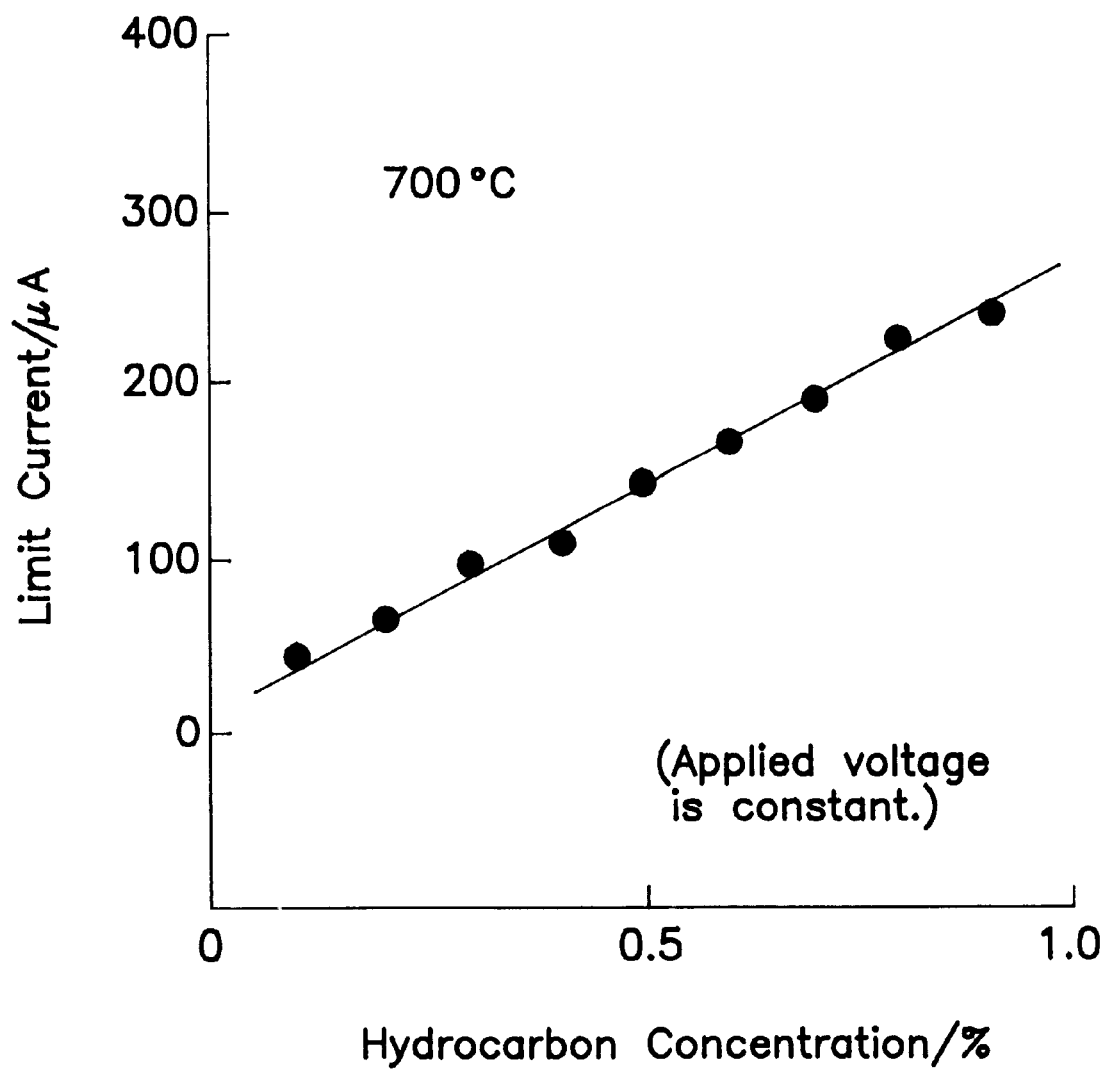
FIG. 7 is a diagram showing the relation of gas concentration and limit current at 700° C. of the sensor in embodiment of the invention.

Varying the gas concentration, the limit current to concentration was investigated at various temperatures. FIG. 7 shows the relation of gas concentration and limit current at 700° C. In a gas concentration range of 0 to 1%, the limit current changed linearly in any gas, and this sensor having the proton diffusion rate determining function was proved to work favorably. The electrolytic voltage was a constant value, and all sample gases could be detected. As compared with the foregoing embodiments in which the electrolytic voltage must be set differently for each type of hydrocarbon, it is a feature of this embodiment that the quantity of hydrogen in hydrocarbons can be measured by one operation.

In this embodiment, Ag-Pd alloy electrode is used as the electrode having the proton diffusion rate determining function, but, aside from Pd and Ag, favorable results were obtained in other electrodes adding Ag or Ru to alloy electrodes of Ti-Mn, Zr-Mn-V, Ca-Ni-, Mg-Ni, La-Ni, etc. In the embodiment, as the electrolyte material, $CaZr_{0.9}In_{0.1}O_{3-\alpha}$ sinter is used, but barium-cerium oxide, strontium-cerium oxide and others may be also employed. Moreover, the shape and fabricating method of electrolyte and electrodes are not limited.

[Embodiment 4]

This embodiment is an example of hydrocarbon sensor characterized by comprising an element capable of generating or moving hydrogen, so as to detect in any atmosphere even in the complete absence of oxygen.

Figure 8:
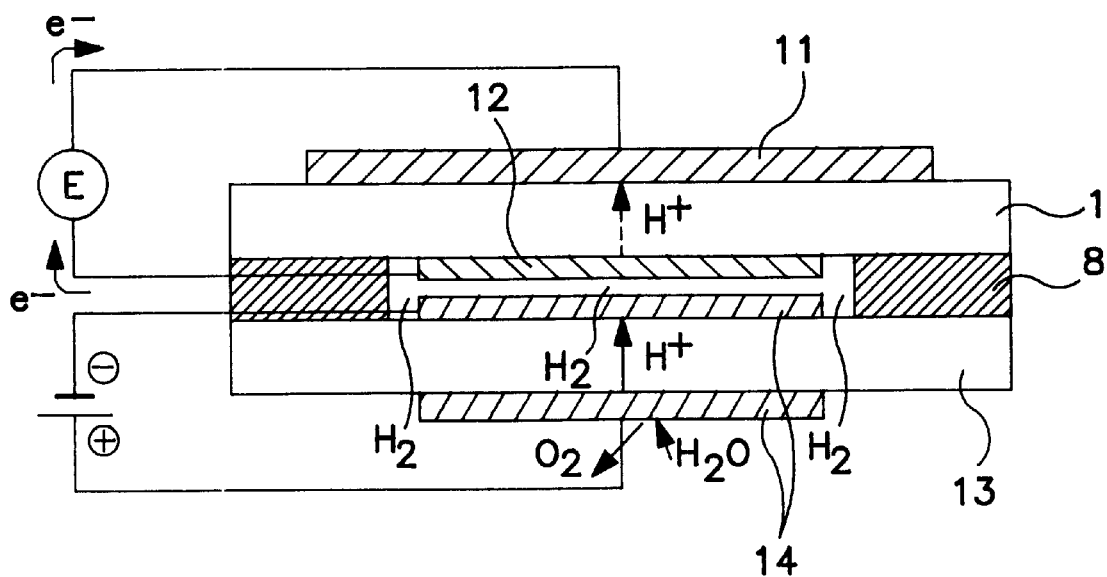
FIG. 8 is a structural diagram of a sensor in embodiment 4 of the invention.

A structure of this sensor is shown in FIG. 8. A solid electrolyte 1 of the sensor element is composed of $BaCe_{0.8}Dy_{0.2}O_{3-\alpha}$ sinter of 10 mm×10 mm×0.5 mm thick, a hydrocarbon active electrode 11 is made of Ag-Pd electrode, an inert electrode 12 is made of gold. An element (hydrogen pump) for generating or moving hydrogen is composed of $CaZr_{0.9}In_{0.1}O_{3-\alpha}$ proton conductive solid electrolyte 13, and a pair of platinum electrodes 14, and the inert electrode side of the sensor was sealed with glass.

This element is heated to 500° C., an electric current is passed into the hydrogen pump in a direction of sending hydrogen into the sensor element (the outer side is positive electrode, the inner side is negative electrode), and the electrode potential of the inert electrode is the hydrogen reference electrode. At this time, in the hydrocarbon active electrode, proton is produced, and an electromotive force is generated between the active electrode and the inert electrode due to hydrogen contrast.

Figure 9:
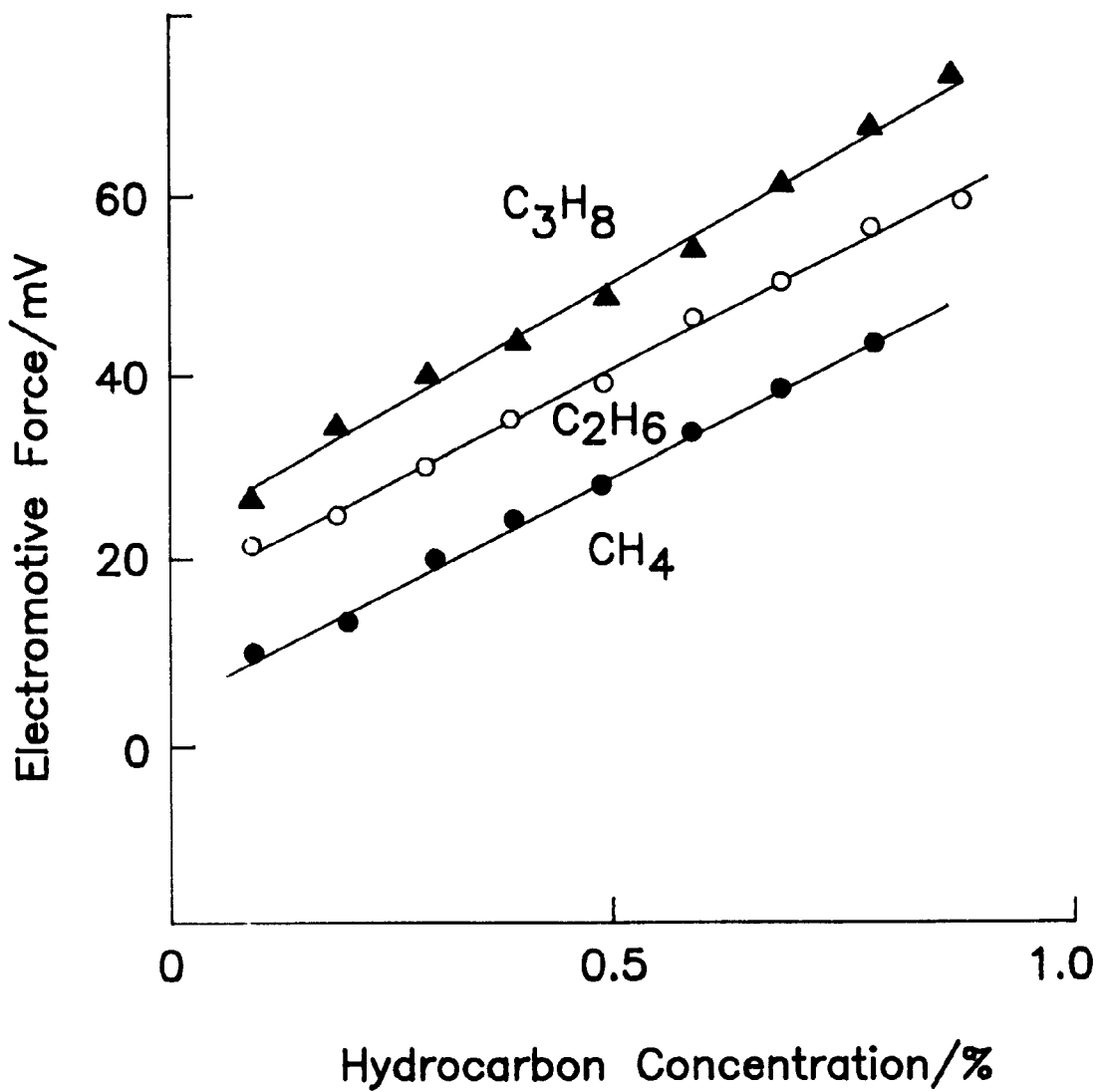
FIG. 9 is a diagram showing the relation of gas concentration and electromotive force of the sensor in the embodiment of the invention.

Using methane, ethane and propane diluted in carbon dioxide as sample gas, each gas was passed through the sensor at flow velocity of 200 cc/min. Varying the gas concentration, the electromotive force to the concentration at various temperatures was investigated. FIG. 9 shows the relation of gas concentration and electromotive force. In a gas concentration range of 0 to 1%, the electromotive force changed linearly in any gas, and this sensor was proved to work favorably in an oxygen-free state. The response was also excellent, and it was about 15 seconds in 90% response.

Hence, obviously, the sensor of the embodiment having the element for detecting hydrocarbons and the element for generating or moving hydrogen was proved to detect hydrocarbon successfully even in the absence of oxygen.

In the embodiment, Ag-Pd is used in the active electrode and gold in the inert electrode, but platinum may be used for the active electrode and copper for the inert electrode, or different combinations may be employed. The shape and fabricating method of electrolyte and electrodes are not limited.

In the foregoing embodiments, the solid electrolyte is composed of $BaCe_{0.8}Gd_{0.2}O_{3-\alpha}$, $BaCe_{0.8}Y_{0.2}O_{3-\alpha}$, and $BaCe_{0.8}Dy_{0.2}O_{3-\alpha}$, but also $BaCe_{0.8}Sm_{0.2}O_{3-\alpha}$ or $BaCe_{0.8}Tb_{0.2}O_{3-\alpha}$, or the like may be employed. Of course, the electrodes of platinum, silver, gold or palladium used in these examples may be mixtures with other components, and the shape and synthesizing method are not limited, and methods of synthesizing and manufacturing the electrolyte and diffusion rate determining layer may include coating method, vapor deposition sputtering method, CVD method, etc.

The voltage and current applied to the cell and device are not limited to shown examples, and the sensor operating temperature is not specified.

In embodiments 2 and 4, the sealing material may be either ceramics or glass.

Of course, the sensor shape, size, manufacturing method, and working method are not particularly specified.

As clear from the description herein, the invention presents a small, handy, and inexpensive sensor that is selective, and high in sensitivity and reliability in any atmosphere (free from effects of oxygen concentration). Therefore, the hydrocarbon sensor of the invention is usable as hydrocarbon detector in living environments or hydrocarbon concentration detector of combustion exhaust gas from automotive engine, stove or other combustion appliance.

What is claimed is:

1. A solid hydrocarbon sensor comprising in combination:
   an inert electrode and an active electrode held in spaced apart relationship by
   a proton conductive solid electrolyte,
   said proton conductive solid electrolyte being of a barium-cerium oxide, whereby when said sensor is exposed to a hydrocarbon, said hydrocarbon reacts with oxygen at said active electrode to generate steam resulting in an electromotive force detectable between said electrodes, the magnitude of the electromotive force being directly related to the concentration of hydrocarbon at said sensor.

2. A hydrocarbon sensor according to claim 1, wherein the barium-cerium oxide contains a rare earth element as a third element.

3. A hydrocarbon sensor according to claim 2, wherein the rare earth element is gadolinium.

4. A hydrocarbon sensor according to claim 1, wherein a material selected from the group consisting of Pt, Au, Ag, Pd, copper and mixtures thereof is used for at least one electrode.

5. A hydrocarbon sensor according to claim 1, wherein one of palladium, platinum, or ruthenium is used as the active electrode material and one of gold or copper is used as the inert electrode material.

6. A hydrocarbon sensor comprising in combination:
   a pair of electrodes,
   a proton conductive solid electrolyte of barium-cerium-rare earth oxide separating said electrodes into an anode and cathode, and
   a hydrocarbon diffusion rate determining layer whereby, a hydrocarbon concentration is detected by a current generated by proton flow in the solid electrolyte under constant potential electrolysis.

7. A hydrocarbon sensor comprising in combination:
   a first anode electrode;
   a proton conductive solid electrolyte of a material selected from the group consisting of calcium-zirconium oxide, barium-cerium oxide, and strontium-cerium oxide with an optional rare earth element component; and a second electrode active to hydrogen and having a proton diffusion rate determining function, whereby hydrocarbon concentration is detected by a current generated by proton flow in the solid electrolyte under constant potential electrolysis.

8. A hydrocarbon sensor according to claim 7, wherein the electrode having proton diffusion rate determining function is made from a hydrogen permeable material.

9. A hydrocarbon sensor according to claim 8, wherein the hydrogen permeable material contains at least one element selected from the group consisting of Pd, Ag, Pt, Ru, Ti, V, Ca, Mg, Mn, Cu, Ni, Zr, and La.

10. A hydrocarbon sensor according to claim 7, wherein the proton conductive solid electrolyte is composed of a material selected from the group consisting of barium-cerium oxide, calcium-zirconium oxide, and strontium-cerium oxide.

11. An electromotive force generating hydrocarbon sensor comprising in combination:

a sensor element for detecting hydrocarbon consisting of a pair of sensor element electrodes spaced apart by a sensor element solid electrolyte, one of said sensor element electrodes being inert and the other sensor element electrode being active, and an element for generating or moving hydrogen to one of the electrodes, said element for generating or moving hydrogen consisting of a pair of hydrogen element generating electrodes spaced apart by a proton conductive solid electrolyte, one of said electrodes and said proton conductive solid electrolyte juxtaposed to said inert sensor element electrode of said sensor element and sealed thereto with glass.

12. An electromotive force generating hydrocarbon sensor comprising in combination:

a sensor element for detecting hydrocarbon consisting of a pair of sensor element electrodes spaced apart by a sensor element solid electrolyte, one of said sensor element electrodes being inert and the other sensor element electrode being active, and an element for generating or moving hydrogen to one of the electrodes, said element for generating or moving hydrogen consisting of a pair of hydrogen element generating electrode spaced apart by a solid electrolyte being a proton conductive oxide, one of said electrodes and said proton conductive oxide solid electrolyte juxtaposed to said inert sensor element electrode of said sensor element and sealed thereto with glass.

13. An electromotive force generating hydrocarbon sensor comprising in combination:

a sensor element for detecting hydrocarbon consisting of a pair of sensor element electrodes spaced apart by a sensor element solid electrolyte, one of said sensor element electrodes being inert and the other sensor element electrode being active, and an element for generating or moving hydrogen to one of the electrodes, said element for generating or moving hydrogen consisting of a pair of hydrogen element generating electrode space apart by a solid electrolyte being a proton conductive oxide composed of a material selected from the group consisting of barium-cerium oxide, calcium-zirconium oxide, and strontium-cerium oxide, one of said electrode and said proton conductive oxide juxtaposed to said inert sensor element electrode of said sensor element and sealed thereto with glass.

* * * * *